US010803143B2

(12) United States Patent
Kamen et al.

(10) Patent No.: US 10,803,143 B2
(45) Date of Patent: Oct. 13, 2020

(54) VIRTUAL BIOPSY TECHNIQUES FOR ANALYZING DISEASES

(71) Applicant: Siemens Healthcare GmbH, Erlangen (DE)

(72) Inventors: Ali Kamen, Skillman, NJ (US); Noha El-Zehiry, Plainsboro, NJ (US); David Liu, Richardson, TX (US); Dorin Comaniciu, Princeton Junction, NJ (US); Atilla Peter Kiraly, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 658 days.

(21) Appl. No.: 15/223,927

(22) Filed: Jul. 29, 2016

(65) Prior Publication Data
US 2017/0032090 A1   Feb. 2, 2017

Related U.S. Application Data

(60) Provisional application No. 62/198,723, filed on Jul. 30, 2015.

(51) Int. Cl.
| | |
|---|---|
| G06F 19/00 | (2018.01) |
| G06N 7/00 | (2006.01) |
| G16H 10/60 | (2018.01) |
| G16H 50/20 | (2018.01) |
| G06N 20/00 | (2019.01) |

(52) U.S. Cl.
CPC ........... G06F 19/321 (2013.01); G06N 7/005 (2013.01); G06N 20/00 (2019.01); G16H 10/60 (2018.01); G16H 50/20 (2018.01)

(58) Field of Classification Search
CPC ........ G16H 50/20; G16H 10/60; G06F 19/34; G06F 19/3418; G06F 16/285; G06K 2209/05; G06N 20/00; G06N 7/005
See application file for complete search history.

(56) References Cited

U.S. PATENT DOCUMENTS

| | | |
|---|---|---|
| 7,949,173 B2 | 5/2011 | Zhou et al. |
| 8,004,563 B2 * | 8/2011 | Talmon .................... G06K 9/00 348/155 |
| 8,386,015 B2 | 2/2013 | Kamen et al. |
| | (Continued) | |

OTHER PUBLICATIONS

Dhawan et al., A Computational Modeling Approach for Deriving Biomarkers to Predict Cancer Risk in Premalignant Disease, p. 283-295, Feb. 2016. (Year: 2016).*

(Continued)

*Primary Examiner* — Kamran Afshar
*Assistant Examiner* — Marshall L Werner (57) ABSTRACT

A computer-implemented method for deriving biopsy results in a non-invasive manner includes acquiring a plurality of training data items. Each training data item comprises non-invasive patient data and one or more biopsy derived scores associated with an individual. The method further includes extracting a plurality of features from the non-invasive patient data based on the one or more biopsy derived scores and training a predictive model to generate a predicted biopsy score based on the plurality of features and the one or more biopsy derived scores.

16 Claims, 7 Drawing Sheets

(56) References Cited

U.S. PATENT DOCUMENTS

| | | | |
|---|---|---|---|
| 8,478,023 B2* | 7/2013 | Kaus | G06T 7/60 |
| | | | 345/419 |
| 8,811,701 B2 | 8/2014 | Khurd et al. | |
| 9,478,022 B2 | 10/2016 | Kamen et al. | |
| 2007/0014462 A1 | 1/2007 | Rousson et al. | |
| 2016/0260211 A1* | 9/2016 | Gillies | G06T 7/41 |
| 2017/0116387 A1 | 4/2017 | El-Zehiry | |
| 2018/0276856 A1* | 9/2018 | Schieke | G06T 11/008 |

OTHER PUBLICATIONS

Roth et al., Anatomy-Specific Classification of Medical Images Using Deep Convolutional Nets, Apr 2015. (Year: 2015).*

Cruz-Roa et al., A Deep Learning Architecture for Image Representation, Visual Interpretability and Automated Basal-Cell Carcinoma Cancer Detection, Medical Image Computing and Computer-Assisted Intervention—MICCAI 2013, 2013. (Year: 2013).*

Saritas, Ismail, Prediction of Breast Cancer Using Artificial Neural Networks, J Med Syst (2012); 36, p. 2901-2907, 2011. (Year: 2011).*

Citak-Er et al., Final Gleason Score Prediction Using Discriminant Analysis and Support Vector Machine Based on Preoperative Multiparametric MR Imaging of Prostate Cancer at 3T, BioMed Research International vol. 2014, p. 1-9, 2014. (Year: 2014).*

Wang et al., Enabling Smart Personalized Healthcare: A Hybrid Mobile-Cloud Approach for ECG Telemonitoring, IEEE Journal of Biomedical and Health Informatics, vol. 18 No. 3, pp. 739-745, May 2014. (Year: 2014).*

Woodfield, Courtney A., et al. "Diffusion-weighted MRI of peripheral zone prostate cancer: comparison of tumor apparent diffusion coefficient with Gleason score and percentage of tumor on core biopsy." American Journal of Roentgenology 194.4 (2010): W316-W322.

Wetter, Axel, et al. "Evaluation of the PET component of simultaneous [18 F] choline PET/MRI in prostate cancer: comparison with [18 F] choline PET/CT." European journal of nuclear medicine and molecular imaging 41.1 (2014): 79-88.

Souvatzoglou, Michael, et al. "Comparison of integrated whole-body [11 C] choline PET/MR with PET/CT in patients with prostate cancer." European journal of nuclear medicine and molecular imaging 40.10 (2013): 1486-1499.

Hartenbach, Markus, et al. "Combined PET/MRI improves diagnostic accuracy in patients with prostate cancer: a prospective diagnostic trial." Clinical Cancer Research 20.12 (2014): 3244-3253.

De Perrot, Thomas, et al. "Potential of hybrid 18 F-fluorocholine PET/MRI for prostate cancer imaging." European journal of nuclear medicine and molecular imaging 41.9 (2014): 1744-1755.

http://www.healthcare.siemens.com/magnetic-resonance-imaging/mr-pet-scanner/biograph-mmr; 2019; retrieved from the Internet.

Loeb, et al.; "The Prostate Health Index: a new test for the detection of prostate cancer." Therapeutic advances in urology 6.2 (2014): 74-77.

Novak, et al.; "Non-invasive Gleason Score using Dynamic PET Image Data", U.S. Appl. No. 62/047,836, filed Sep. 9, 2014.

Boykov, Yuri Y., and M-P. Jolly. "Interactive graph cuts for optimal boundary & region segmentation of objects in ND images." Proceedings eighth IEEE international conference on computer vision. ICCV 2001. vol. 1. IEEE, 2001.

Grady, Leo "Random Walks for Image Segmentation"; . In IEEE Transactions on Pattern Analysis and Machine Intelligence, vol. 28, No. 11, Nov. 2006 (pp. 1-17).

Noha El-Zehiry, Prasanna Shaoo and Adel Elmaghraby, "Combinatorial Optimization of the piecewise constant Mumford-Shah functional with application to scalar/vector valued and volumetric image segmentation," Computer vision and Image Understanding, May 2011.

Chan, Tony F., and Luminita A. Vese. "Active contours without edges." IEEE Transactions on image processing 10.2 (2001): 266-277.

Dickinson, Louise, et al. "Magnetic resonance imaging for the detection, localisation, and characterisation of prostate cancer: recommendations from a European consensus meeting." European urology 59.4 (2011): 477-494.

F. C. Ghesu et al., Marginal Space Deep Learning: Efficient Architecture for Detection in Volumetric Image Data, MICCAI 2015.

www.healthcare.philips.com/main/products/nuclearmedicine/products/ingenuity_tf_pet_mr/; retrieved from the Internet Apr. 3, 2019.

* cited by examiner

VIRTUAL BIOPSY TECHNIQUES FOR ANALYZING DISEASES

CROSS-REFERENCE TO RELATED APPLICATIONS

This application claims the benefit of U.S. Provisional Patent Application Ser. No. 62/198,723, filed on Jul. 30, 2015, entitled "A Biopsy-Free Method and System based on Highly-Specific Imaging for Analyzing Lesions and Cancer," the entirety of which is incorporated by reference herein.

TECHNICAL FIELD

The present disclosure relates generally to biopsy-free techniques for analyzing diseases based on patient data acquired in a non-invasive manner. The technique described herein may be used, for example, in the detection of lesions and cancer without a biopsy.

BACKGROUND

Biopsy is an invasive clinical procedure wherein tissue is removed from a living body and examined to determine the presence, cause, or extent of a disease. Typically, a tissue sample is examined by a pathologist who provides a reading report with relevant findings. For example, in the case of prostate cancer, the Gleason score is used to determine the aggressiveness of the disease; cancers with higher Gleason score are more aggressive and have a worse prognosis.

In many cases, biopsy is the first stage in a clinical evaluation and treatment plan that eventually utilizes imaging modalities such as Magnetic Resonance Imaging (MRI) to apply curative techniques or perform active surveillance on a region of interest to confirm the grade and extent of a disease. Additionally, even when an initial biopsy is negative, if a test results in elevated markers for a disease, specialized imaging may be performed in an attempt to detect the disease.

One drawback of performing biopsies is that it is often difficult to acquire samples from all the areas around the tumor. For example, in the case of prostate cancer, it is particularly difficult to sample the peripheral zone where cancer most frequently occurs. Inaccurate sampling results in false readings since results depend on the location from which the tissue sample is acquired. In some cases, the biopsy score results are inconclusive because the tissue is sampled from the wrong location. Additionally, biopsies may entail complications such as hemorrhage, bleeding, pain, risk of infection and sepsis, all of which may result in hospital readmissions and mortalities.

SUMMARY

Embodiments of the present invention address and overcome one or more of the above shortcomings and drawbacks by providing methods, systems, and apparatuses related to a "virtual" biopsy methodology which uses a predictive model to obtain biopsy results based on imaging data and other patient data acquired in a non-invasive manner. The techniques described herein may be applied, for example, to determine the presence, cause, or extent of cancers and other diseases.

According to some embodiments, a computer-implemented method for deriving biopsy results in a non-invasive manner includes acquiring a plurality of training data items. Each training data item comprises non-invasive patient data and one or more biopsy derived scores associated with an individual. The method further includes extracting features from the non-invasive patient data based on the biopsy derived scores and training a predictive model to generate a predicted biopsy score based on the features and the biopsy derived scores. As new non-invasive patient data corresponding to a new individual is acquired, new features may be extracted and used to generate a predicted biopsy score for the new individual by applying the predictive model to the plurality of new features. In some embodiments, the new non-invasive patient data includes one or more images. A disease probability map may be generated for the individual by applying the predictive model to the new features. This disease probability map may then be overlaid over the images.

In some embodiments of the aforementioned method, the non-invasive patient data includes one or more medical image. In these embodiments, prior to extracting the features, organs associated with a particular disease maybe segmented in the medical images. The features can then be extracted based on the segmented organ. Additionally (or alternatively), the medical images may be localized to a region of interest associated with the particular disease prior to extracting the features. The features can then be extracted based on the region of interest.

The aforementioned method may have various enhancements, refinements, or other modifications in different embodiments of the present invention. For example, in one embodiment, the features are automatically generated by applying a deep learning technique to the training data items. In another embodiment, the features are manually specified by one or more users. As described above, the non-invasive patient data may include medical images; but, it may also include data about the individual such as clinical information, demographic data, and/or in-vitro diagnostic data. Additionally, in some embodiments, the training items are synthetically augmented by applying deformations within reasonable anatomically and bio-mechanical extents.

According to other embodiments, a second method for deriving biopsy results in a non-invasive manner includes an image scanner device acquiring medical images of an anatomical area of interest. These medical images may comprise, for example, anatomical and/or functional images acquired using a multi-parametric Magnetic Resonance/Positron Emission Tomography acquisition. One or more computer systems extract features from the images and generate a predicted biopsy score for a disease by applying a predictive model to the features. For example, where the disease is prostate cancer, the predicted biopsy score may comprise a Gleason score. In some embodiments, an organ of interest in the medical images is segmented into a plurality of organ segments and the predicted biopsy score is generated based on these segments. For example, the predicted biopsy score may be generated by (a) determining a local biopsy score for each of the segments using the predictive model and (b) combining the local biopsy scores to generate the predicted biopsy score.

According to another aspect of the present invention, a system for deriving biopsy results in a non-invasive manner comprises an image scanner device configured to acquire one or more medical images of an anatomical area of interest and one or more computer systems. Each computer system comprises one or more non-transitory, tangible computer-readable mediums holding computer-executable instructions for extracting features from the medical images and generating a predicted biopsy score by applying a predictive model to the features. The computer systems further include one or more processors which are configured to execute the aforementioned computer-executable instructions.

In some embodiments of the aforementioned system, these computer systems are located in the image scanner device, while in other embodiments, the computer systems and the image scanner device are physically separated (e.g., connected via a computer network). Additionally, hybrid computing systems which use computing resources on the scanner in conjunction with remote computing resources may be employed. For example, in one embodiment, feature extraction is performed by a first computer located in the image scanner device and generation of the predicted biopsy score is performed at a second computer that is physically separated from the image scanner device.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawing. For the purpose of illustrating the invention, there is shown in the drawing embodiments that are presently preferred, it being understood, however, that the invention is not limited to the specific instrumentalities disclosed. Included in the drawing are the following Figures.

DETAILED DESCRIPTION

The following disclosure describes the present invention according to several embodiments directed at methods, systems, and apparatuses related to techniques for a "virtual" biopsy methodology which applies a predictive model to obtain biopsy-derived information in a non-invasive manner. Briefly, the predictive model is trained using real biopsy data and features such as anatomical information, functional information, blood diagnostic data and patient demographics. Once trained, the model can be applied to a new set of features to derive information that would traditionally be generated by a biopsy. In the following, prostate cancer is used as an example to describe the techniques involved in virtual biopsy; however, it should be understood that the same concepts and methodology can be applied to other cancer types or surgical based decisions as well.

Figure 1:
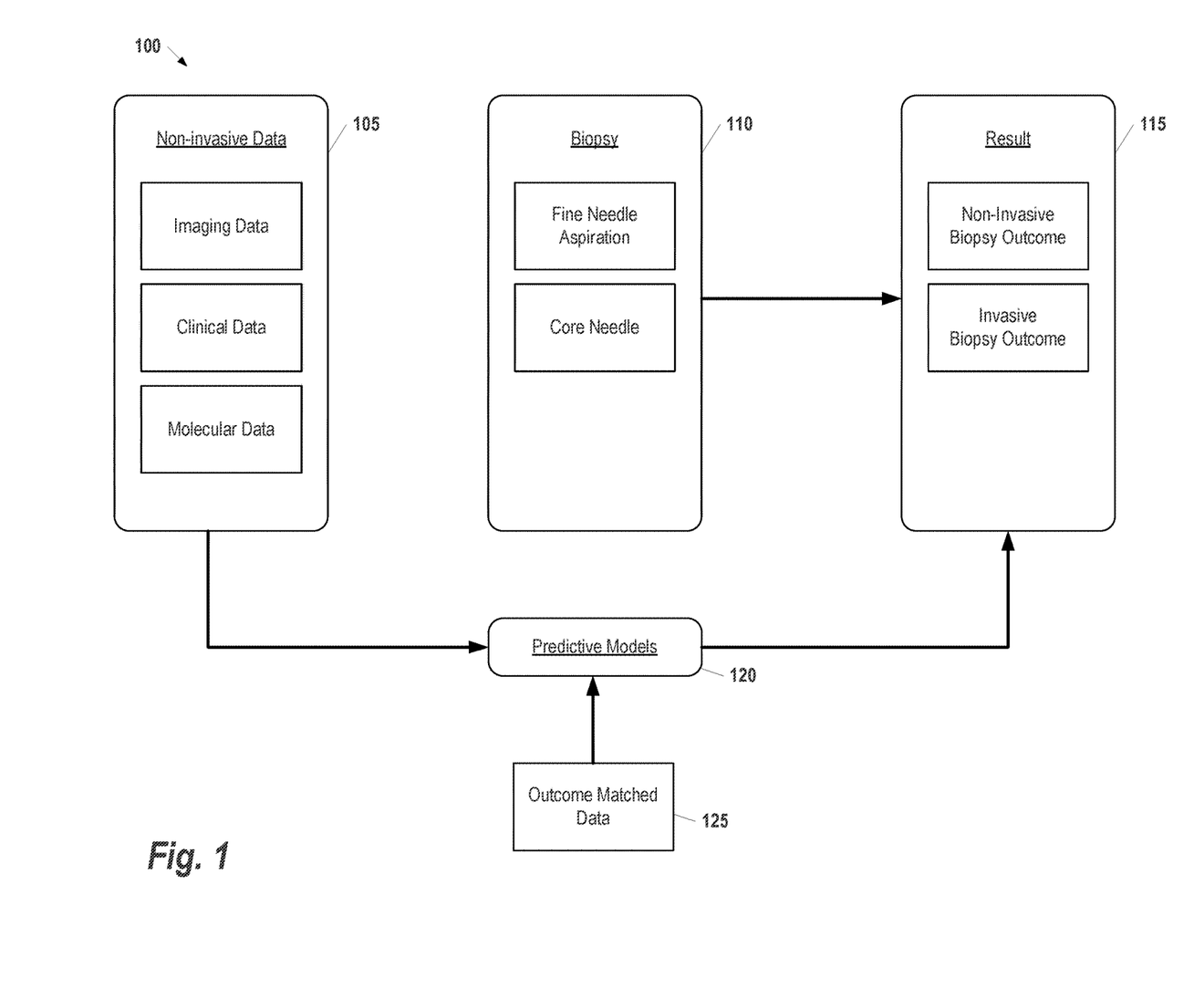
FIG. 1 provides a high-level overview of a virtual biopsy system which can predict biopsy results through non-invasive measures, according to some embodiments.

FIG. 1 provides a high-level overview of a virtual biopsy system 100 which can predict biopsy results through non-invasive measures, according to some embodiments of the present invention. In this example, Non-Invasive Data 105 is acquired prior to a biopsy. As shown in FIG. 1, the Non-Invasive Data 105 includes imaging data, clinical data, and molecular data; however, it should be understood that, in general, any type of relevant patient medical information may be utilized as the Non-Invasive Data 105. This Non-Invasive Data is used as input to Predictive Models 120 which are trained based on Outcome Matched Data 125. These Predictive Models 120 output a non-invasive biopsy outcome in the Results 115. This non-invasive biopsy outcome provides the same information as would be provided by a real biopsy, through the use of just the Non-Invasive Data 105.

The predictive model used in the Predictive Models 120 may be trained based on various features derived from the Non-Invasive Data 105. In addition, any linear or nonlinear combination of the subsets of features may also be used for the training and testing. In some embodiments, the Predictive Models 120 comprise a deep learning system that generates novel features automatically from data. In the training phase, all the aforementioned features can be provided as input to the Deep Learning system during training. Moreover, in some embodiments, the Predictive Models 120 may include several different classifiers trained based on different subsets of features or different combination of features to accommodate any missing features in the execution phase. Moreover, rules may be enforced for the classifier choice in the execution phase or a weighted combination (linear or nonlinear combination) of the results of multiple classifiers may be used to obtain the non-invasive biopsy outcome included in the Results 115. Moreover, additional training data beyond the non-invasive data and tumor outcome can be synthetically generated. Additional synthetic images with virtual organs and tumors can be generated by several methods of different complexities with the following steps: starting from a real patient image, it is deformed, warped, and resized within anatomically reasonable extent. The deformations can be defined mathematically such as affine transformation, or can be noisy and random. Alternatively, an organ/tumor contours either manually or automatically marked, and then within anatomically reasonable extent, we deform, warp, and resize the organ/tumor contours. The deformations can be defined by bio-mechanically correct models. Finally, the synthesized images are then added into the training database.

Depending on the non-invasive biopsy outcome generated using the Predictive Models 120, an actual Biopsy 110 may be performed using one or more techniques known in the art (e.g., fine needle aspiration, core needle, etc.). For example, a virtual biopsy outcome which is positive may be verified by performing the Biopsy 110. The Biopsy 110 generates invasive biopsy outcome in the Results 115 which may be used to verify, supplement, or replace the non-invasive biopsy outcome generated by the Predictive Models 120.

It should be noted that the virtual biopsy system 100 shown in FIG. 1 provides some benefits not available in traditional (i.e., not virtual) biopsy systems. For example, in the context of prostate cancer assessment, a Gleason score is a measurement which grades prostate cancer tissue based on how it looks under a microscope. One of the major challenges associated with Gleason scoring is that the results depend on the location from which the tissue sample is acquired. In some cases, the biopsy/Gleason score results are inconclusive because the tissue is sampled from the wrong location. The virtual biopsy techniques described herein enhance the conventional biopsy by analyzing a much larger region of interest (ROI), as well as other patient information not ordinarily considered by traditional biopsies, to derive the Gleason score.

Figure 2:
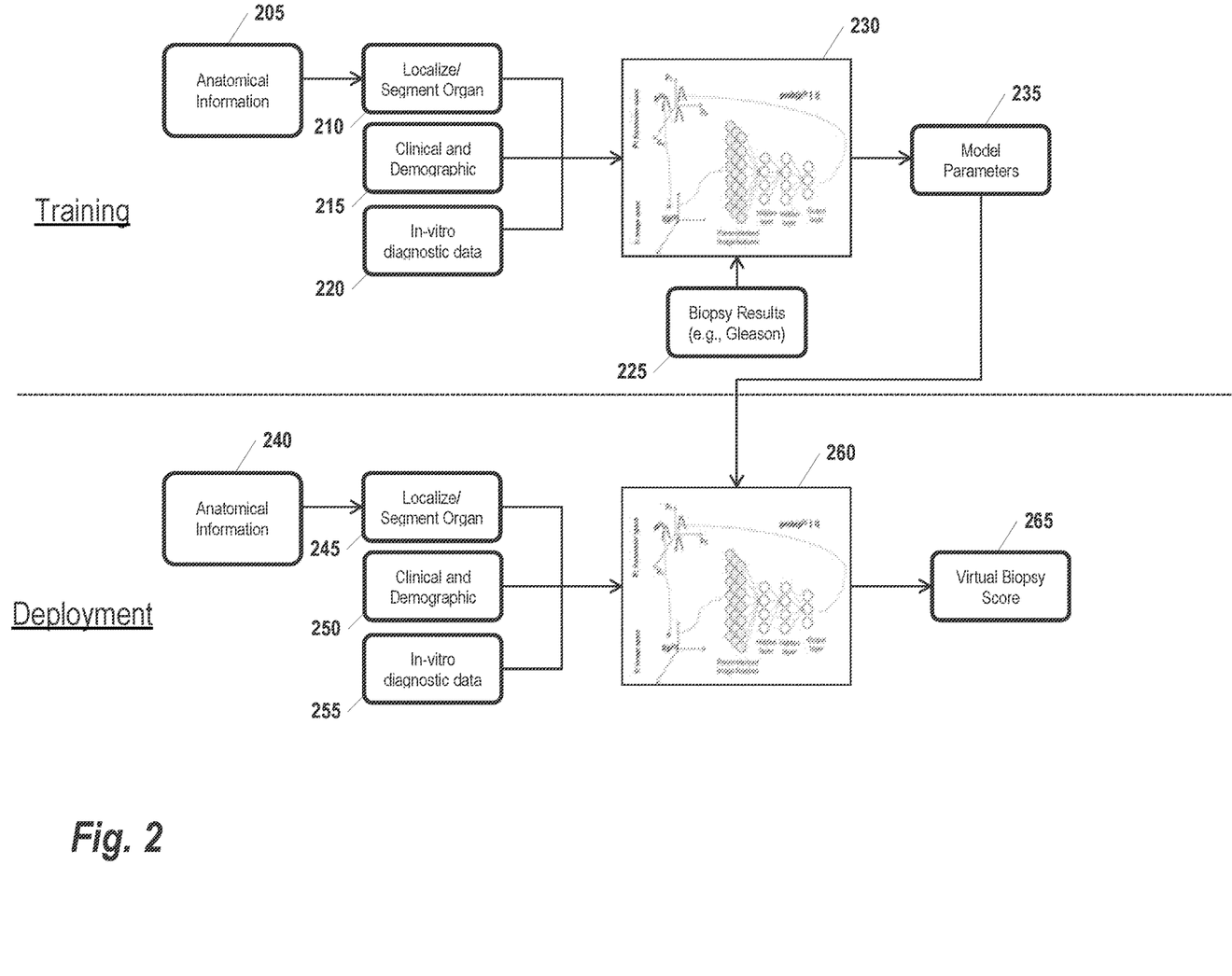
FIG. 2 provides a more detailed overview of the virtual biopsy system, in training deployment stages, according to some embodiments.

FIG. 2 provides a more detailed overview of the virtual biopsy system, in training and deployment stages, according to some embodiments. The top portion of FIG. 2 illustrates the training stage. The initial input during this stage is Anatomical Information 205 comprising one or more images. This Anatomical Information 205 may be acquired from one or more imaging modality generally known in the art including, without limitation, Computed Tomography (CT), Magnetic Resonance Imaging (MRI), Ultrasound (US), and Optical Coherence tomography (OCT), technology. The Anatomical Information 205 may further comprise functional information derived from imaging modalities such as Positron Emission Tomography (PET), Single Photon Emission Computed Tomography (SPECT), Dynamic Contract Enhanced Magnetic Resonance Imaging (DCE-MRI), Diffusion Weighted Magnetic Resonance Imaging (DW-MRI). Once acquired, the image data in the Anatomical Information 205 is segmented using manually, automated, or semi-automated techniques generated in the art to produce a Segmented Organ 210.

In some embodiments, the Anatomical Information 205 comprises Multi-Parametric MRI data. Multi-Parametric MRI provides valuable information for tissue characterization. There exists large clinical evidence regarding the utility of multi-parametric MRI in detecting and localizing cancer; thus it can be used as a valuable source of information for performing virtual biopsies. Moreover, the scoring system for prostate cancer combines and distills information from multiple MRI exams and is relatively subjective. Despite such limitations, guidelines in both Europe and United States call for MRI exams as an additional test for biopsy negative patients, showing the value of multi-parametric MRI.

In some embodiments, the Anatomical Information 205 is obtained using a simultaneous acquisition of anatomical/functional images with combined modalities such as PET/CT and more recently PET/MR (e.g., Siemens mmR Scanner, Philips TF Ingenuity PET/MR). For example, in one embodiment, a multi-parametric MR/PET acquisition may be utilized that provides anatomical as well as functional information; however, it should be understood that any other combination of modalities can be used.

As one example of Multi-Parametric MRI, 4D Imaging (perfusion) may be used in some embodiments to provide pharmacokinetic information and other valuable tumor information. The workflow for implementing 4D Imaging may vary; although, in principle, any imaging workflow can be used with the virtual biopsy techniques described herein. For example, the recommended Siemens Tissue 4D workflow includes a DCE-MRI with fixed flip angle; using re-contrast series with variable flip angle to calculate the T1-map; and acquiring corresponding morphological images. Spectroscopy may provide yet another source of information.

Continuing with reference to FIG. 2, the Segmented Organ 210 is used as input to a Predictive Model 230 (illustrated in FIG. 2 as a Deep Learning model). In the example of FIG. 1, a Clinical and Demographic Data 215 as well as In-vitro Diagnostic Data 220 are used as additional input to the Predictive Model 230. The Predictive Model 230 extracts features based on the Anatomical Information 205 (including the Segmented Organ 210), as well as the Clinical and Demographic Data 215 and the In-vitro Diagnostic Data 220. In some embodiments, machine learning techniques known in the art may be used to automate detection of the features. In other embodiments, a clinician or other user may manually identify and annotate the image features. Based on the imaging modality/modalities used, the extracted features may be binary, numerical, categorical, etc. Additional examples of feature extraction techniques are detailed below in reference to FIG. 4.

For dynamic contrast-enhanced datasets, the Anatomical Information 205 is essentially four dimensional. Some 4D image scanners support workflows which may be used obtain one or more of the following values that can be used as features in the Predictive Model 230: Tofts model K_trans (transfer constant), V_e (extra-vascular extra-cellular volume fraction), K_ep (reflux constant), wash-in (enhancement in the tissue due to contrast uptake), wash-out, time-to-peak (i.e., time until the contrast enhancement reaches the highest concentration and wash-out starts), arrival time (i.e., time when contrast enhancement starts), positive enhancement integral (the value of concentration when the contrast enhancement reaches its highest concentration and wash-out starts), and the Initial Area under Curve in 60 seconds.

Figure 3:
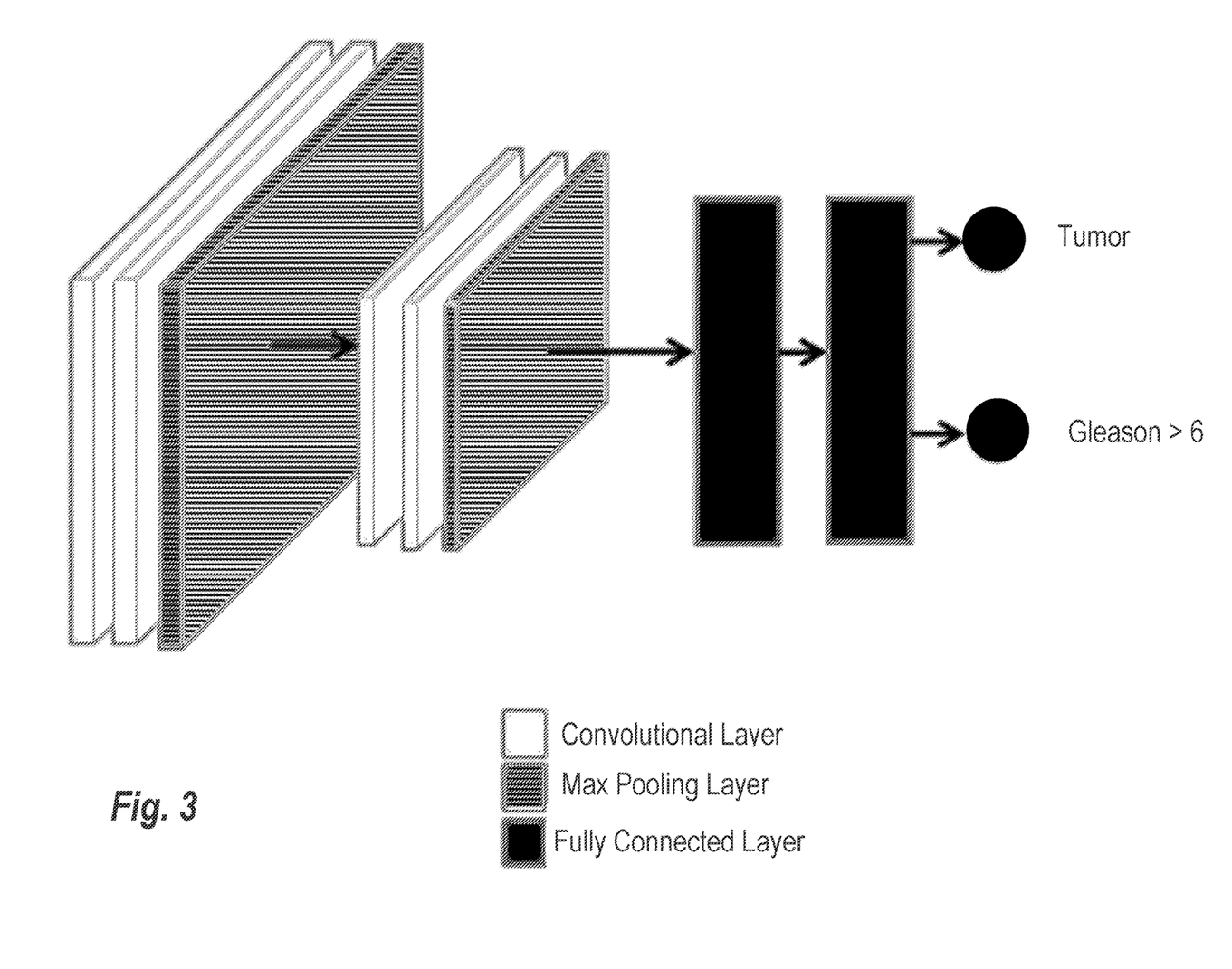
FIG. 3 illustrates an example of a deep learning network architecture to determine tumor presence and high Gleason score, according to some embodiments.

In some embodiments, the Predictive Model 230 utilizes a deep learning network that accepts a patch of multi-modal data and determines whether the patch is associated with a tumor and if it has a Gleason score of 7 or greater. FIG. 3 illustrates an example of a deep learning network architecture used to determine tumor presence and high Gleason score, according to some embodiments. The network in the example of FIG. 3 is comprised of two sets of convolutional layers followed by max pooling which feed into two fully connected layers to arrive at a classification. The trained network can be deployed to analyze patches of the registered multi-modal images.

To determine the correspondence of the identified features to disease outcomes during model training, ground truth Biopsy Results 225 are also provided to the Predictive Model 230. The form of the Biopsy Results 225 will depend on the type of disease being analyzed. For example, in the case of pancreatic cancer, the Biopsy Results 225 may comprise a Gleason score.

The training stage results in a set of Model Parameters 235 corresponding to the Predictive Model 230. Following training, the virtual biopsy system is deployed by delivering the Model Parameters 235 to a clinical setting where they are used as input into a Predictive Model 260 which is configured similarly to the Predictive Model 230 used for training. Alternatively, the Predictive Model 230 may be deployed in conjunction with the Model Parameters 235 to yield the Predictive Model 260.

Continuing with reference to FIG. 2, in the clinical setting, new Anatomical Information 240 is acquired and used to create a new Segmented Organ 245. This new Anatomical Information 240 may be acquired using any of the techniques described above with respect to the Anatomical Information 205 used in the training stage. Once the image data is segmented, the Segmented Organ 245 is used as input into a Deployed Predictive Model 260, along with new Clinical and Demographic Data 250 and new In-vitro Diagnostic Data 255. The Deployed Predictive Model 260 then produces a Biopsy Results 265 (in this example a biopsy score) based on the various inputs. In some embodiments, the user specifies the score or quantity to be measured by the Deployed Predictive Model 260, while in other embodiments, the Deployed Predictive Model 260 is pre-configured to generate a particular type of score or quantity. For example, for prostate cancer assessments, the Deployed Predictive Model 260 may be pre-configured to always generate a Gleason score. In some embodiments, a localized Gleason score may be provided for each prostate segments (e.g., varying from 16 segments to 27 segments) in the different prostate zones. In other embodiments, a global Gleason Score may be generated by combining the local Gleason scores in the different segments.

Depending upon the regulatory state, the Deployed Predictive Model 260 may not be able to report an absolute score. As an alternative or supplement to the score, in some embodiments, additional information may be provided which details the basis for the score or other probability-derived information. For example, in one embodiment, a cancer likelihood probability map is overlaid on the original image data based on a regression of the score. The result would be "hot" areas that would be the decision of the operator on how to proceed with additional analysis.

Figure 4:
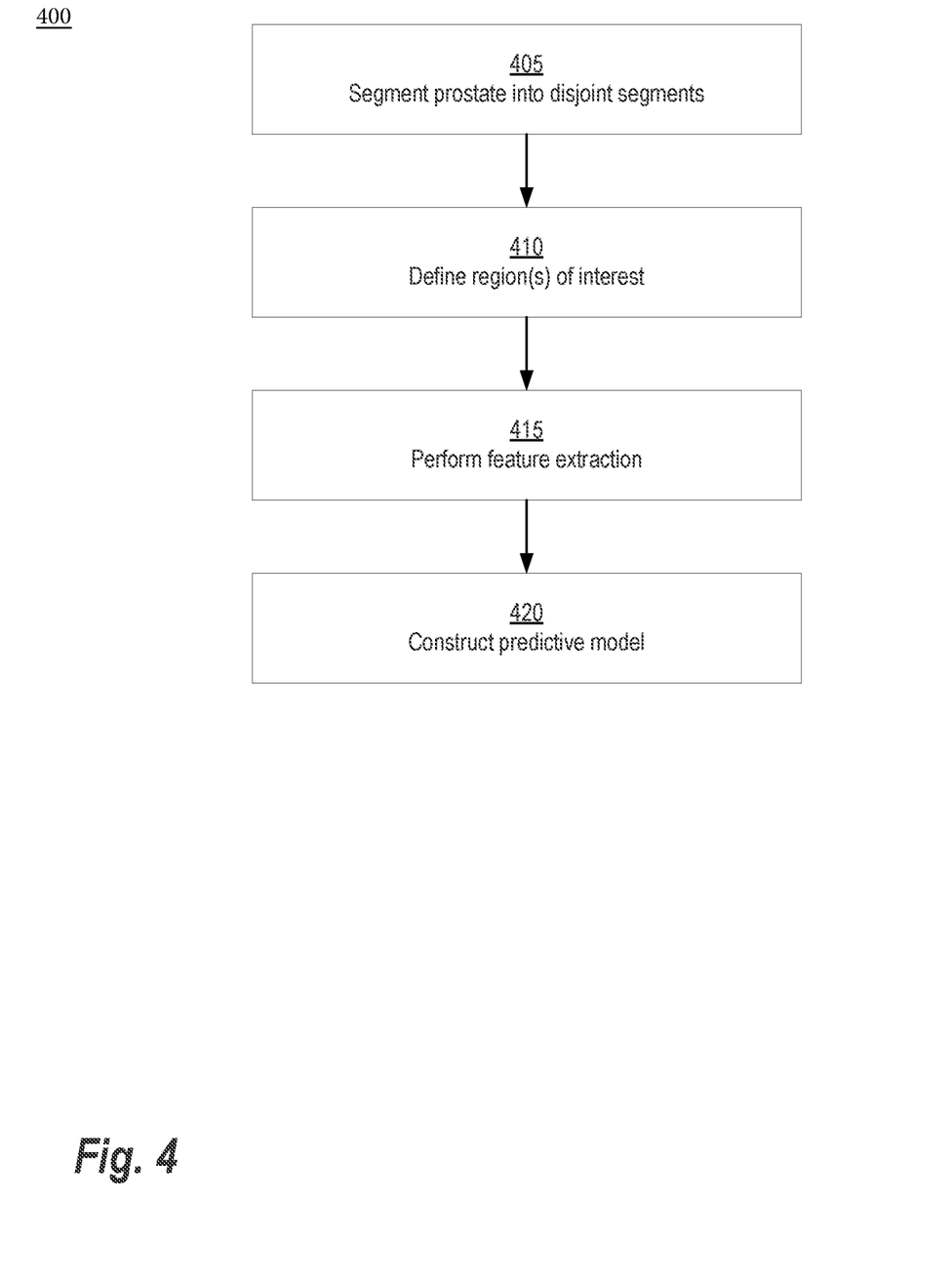
FIG. 4 provides an example method for performing feature extraction, according to some embodiments of the present invention.

FIG. 4 provides an example method 400 for performing feature extraction, according to some embodiments of the present invention. This method 400 may be implemented by one or more computing systems (see, e.g., FIG. 6) based on information received from a medical imaging scanner. The description below focuses on the prostate; however, the same approach is applicable to other organs or anatomical structures as well. The ROI can be the whole prostate, a subset of the prostate where a suspicion of a tumor exists, a partition of the prostate into disjoint sets where each set represents an ROI. Starting at step 405, the prostate is segmented into a plurality of disjoint segments. In some embodiments, the segmentation of the prostate is performed manually where the user interacts with a visualization platform to highlight the prostate boundaries/inner voxels. In other embodiments, the prostate is segmented in a semi-automatic manner where the user highlights only some voxels of the prostate and the segmentation algorithms outputs the full prostate segmentation. In other embodiments, the segmentation is obtained automatically. Examples of segmentation processes that may be used in some embodiments are described in detail in U.S. Pat. No. 9,042,620, issued May 26, 2015 and entitled "Method and system for multi-organ segmentation using learning-based segmentation and level set optimization," the entirety of which is incorporated herein by reference.

Once the prostate is segmented, one or more ROIs are defined at step 410. In some embodiments, the ROI(s) are defined manually, through user interaction with a visualization system and that allows the user to manually draw the region of interest on one or more images. In other embodiments, ROI identification is performed in an automatic or semi-automatic, whereby the user highlights part of the ROI and an imaging based optimization algorithm is used to compute the ROI boundaries based on the image features. Algorithms such as graph cuts, random walk, Mumford-Shah, or Level sets can be used to perform this optimization task. Other segmentation algorithms can be used as well. In other embodiments, ROI identification is performed through anatomical partitioning, wherein the prostate is subdivided into disjoint segments that constitute the different anatomical zones in the prostate. Each segment may be considered an ROI. In some embodiments, localization of a region of interest may be provided based on the localized scores and known image features. The same concept can be applied to other cancer types as well.

Continuing with reference to FIG. 4, at step 415, feature extraction is performed in a manual, semi-automatic, or full automatic manner. A combination of these three methods may also be used, i.e., some of the futures can be input manually by the users while other are calculated semi-automatically based on the interaction. When automatically computing the features, the computer system(s) implementing the method 400 may generate all of the features. For example, the maximum diameter of the ROI (s) will be computed automatically. For manual computation of the features, the user may interact with a visualization platform to draw the maximum diameter in one or more directions of the 4D ROI. For semi-automatic feature identification, a combination of the automatic and manual techniques described above would yield to a semi-automatic feature extraction that utilizes the user interaction to compute some of the features.

Features that can be computed from the ROI include, without limitation, the volume of the ROI, the surface area of the ROI, the diameter of the ROI, or the texture features associated with the ROI (e.g., contrast, correlation, second angular momentum, entropy, local binary pattern, etc.). Additionally, geometric descriptors of the ROI (e.g., mean curvature, Gaussian curvature, curvedness, shape index, etc.) may be used as features. For data acquired using a PET modality, Standard Uptake Value (SUV) may be used as a feature. For data acquired via Diffusion Weighted MR imaging, Apparent Diffusion Coefficient (ADC) and different b-value maps may be used as features.

In some embodiments, additional features are automatically discovered by a Marginal Space Deep Learning (MSDL) or other Connectionist/Deep Neural Network systems. In such a system, image features are not hand-crafted, but rather are data-driven and generated by the computer using specific algorithms such as back-propagation. For example, using techniques generally known in the art, MSDL used for 9D bounding box detection of a particular feature space.

Aside from the ROI, features may be extracted from patient clinical and demographic information and in-vitro diagnostic data (see FIG. 2). For example, in the context of prostate cancer, features may be identified based on a patient's blood test such as Prostate Specific Antigen (PSA) level, PSA velocity, PSA density, and PHI (Prostate Health Index). These features may be supplemented with features identified based on patient demographics such as weight, height age, body mass index (BMI), body surface area (BSA), prostate size, past history of prostate cancer occurrence (if any), past measurements of PSA and PHI test results (if any).

Once the features are extracted, the predictive model is constructed at step 420 using (Deep) Machine Learning. The learning approach used at step 420 may be, for example, fully supervised, semi-supervised, transductive, or reinforcement learning. In some embodiments, a Deep Learning (Deep Neural Network, Connectionist) method is used to build a prediction model or classifier. In Deep Learning, image features are automatically generated rather than hand-crafted. Such features are therefore data-driven and can often outperform human-engineered features. All other hand-crafted features can be provided as additional input to the Deep Learning system. In other embodiments, alternative machine learning methods, such as the Probabilistic Boosting Tree or Decision Forest may be used. In these implementations once the features are extracted and the ground truth is assembled, the computer system(s) implementing the method 400 has all the necessary information to construct the predictive model. For each patient, the computer system may utilize a feature vector comprising the set of extracted features and the Gleason score from the ground truth. The information for all the patients is input into to a machine learning algorithm to learn the mapping between the feature vectors and the scores/quantities of interest (e.g., Gleason score for Prostate cancer).

Figure 5A:
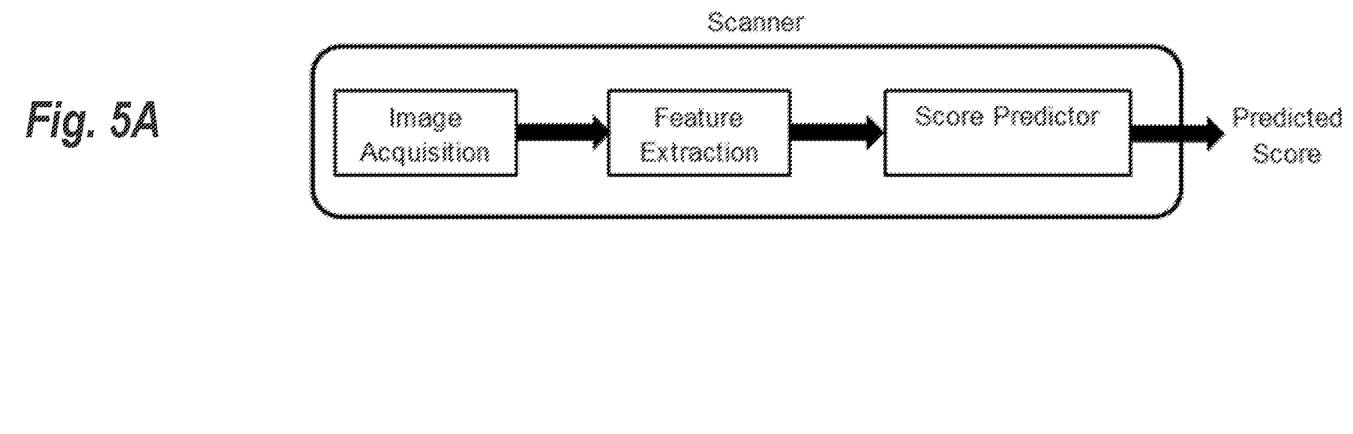
FIG. 5A provides an example workflow used in some embodiments where all processing steps (image acquisition, feature extraction, and score prediction) are performed on the scanner.
Figure 5B:
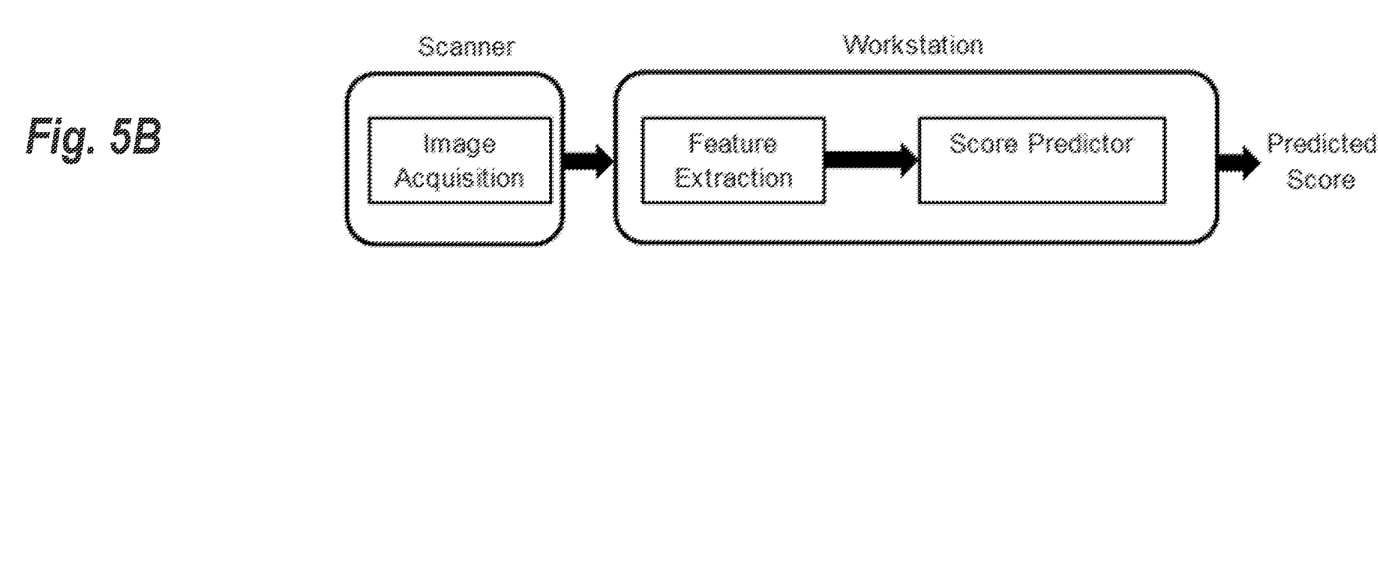
FIG. 5B shows an example workflow used in some embodiments where only image acquisition is performed on the scanner.
Figure 5C:
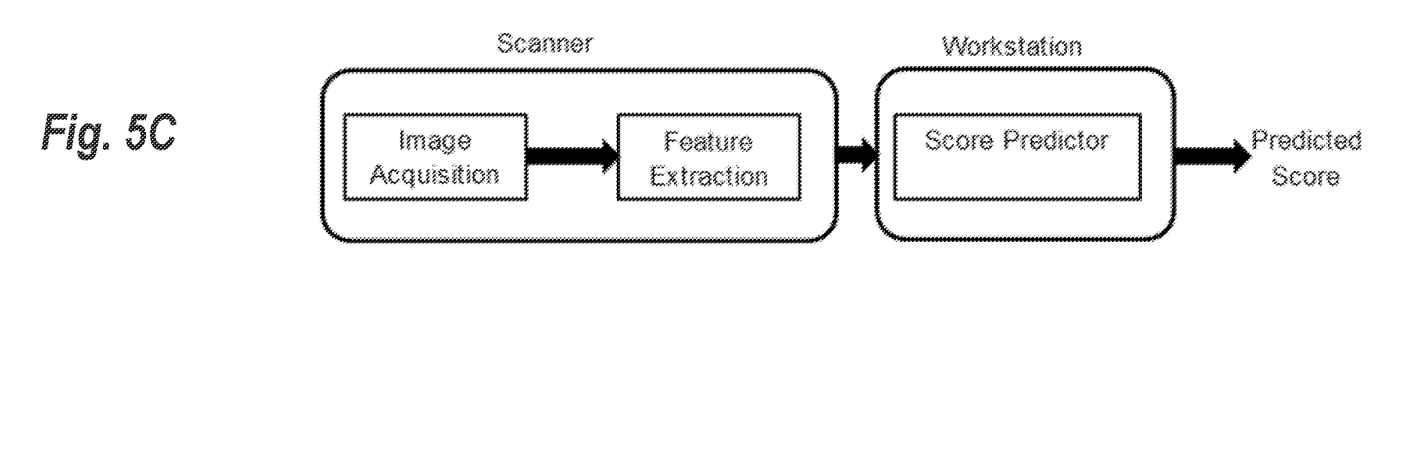
FIG. 5C shows an example workflow used in some embodiments where feature extraction is implemented on the scanner and only score prediction is performed on the workstation.
Figure 5D:
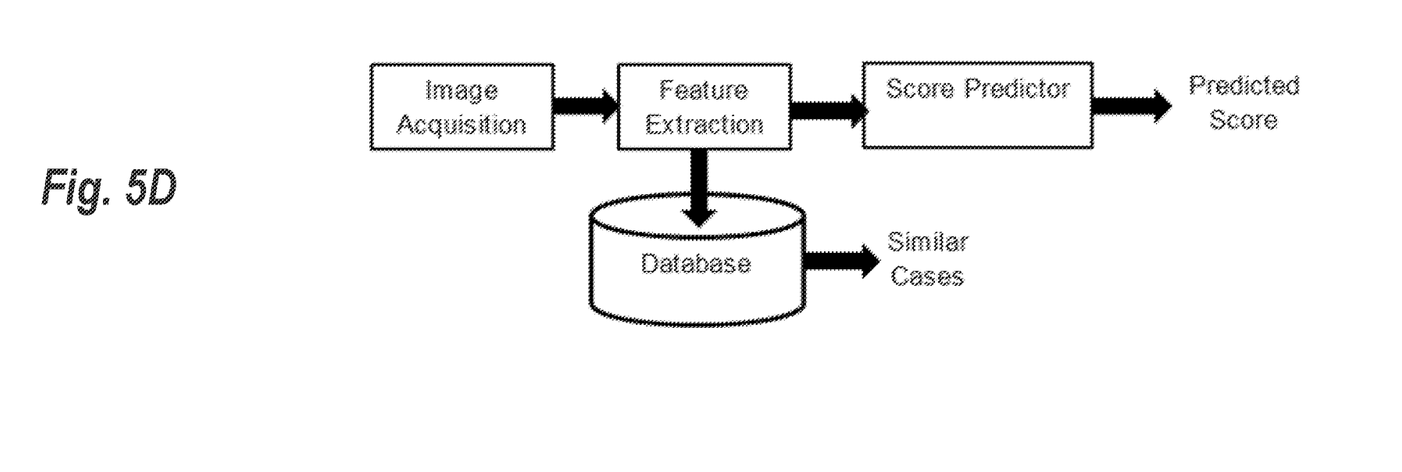
FIG. 5D shows a generic workflow similar to those presented in FIGS. 5A-5C, coupled with a database of previous cases matched against the features extracted to retrieve similar documented cases for the operator to compare against.

FIGS. 5A-5D provide four example workflows that may be used in implementing the techniques described herein. These workflows differ primarily on the amount of computation performed on the scanner versus the computational workstation. In FIG. 5A, all processing steps (image acquisition, feature extraction, and score prediction) are performed on the scanner. In FIG. 5B, only image acquisition is performed on the scanner. The acquired images are then transferred to a computer workstation (local to or remote from the scanner) where feature extraction and score prediction is performed. In some embodiments, the example FIG. 5B may be used in cloud-based architecture where images are delivered over the Internet to a remote computing environment for processing. In FIG. 5C, feature extraction is additionally implemented on the scanner and only score prediction is performed on the workstation. For example, for the prostate cancer analysis, an output feature vector is transferred to the workstation and the virtual Gleason score prediction is performed on the scanner. This allows the amount of information transferred between the scanner and the workstation to be minimized because only the features need to be transferred, rather than the full images. Finally, FIG. 5D shows a generic approach of those presented in FIGS. 5A-5C, coupled with a database of previous cases matched against the features extracted to retrieve similar documented cases for the operator to compare against.

Prostate cancer is particularly interesting because of the challenges associated with the biopsy that cannot consistently provide a uniform sampling of the prostate tissue and because of the very high false positive rate of the PSA test. However, the techniques described herein may be applied to other oncology applications such as breast or lung cancer. For example, the same techniques can be applied to breast cancer and we can engineer the scoring system that is currently used to stage breast cancer based on biology. The techniques can be used to predict the Scarf-Bloom-Richardson Score or the Nottingham histologic score (which is a modification of the Scarf-Bloom-Richardson Score) or any other scoring system that deduces the cancer stage from pathology. For lung cancer, the techniques may be used to predict the tumor, node, and metastasis (TNM) score. For liver cancer, the disclosed techniques can identify the degree of cirrhosis, fatty liver. For all types of cancer, the techniques described herein can predict the histological grade, predict the response to therapy, predict the cancer stage, predict the survival time, etc.

Figure 6:
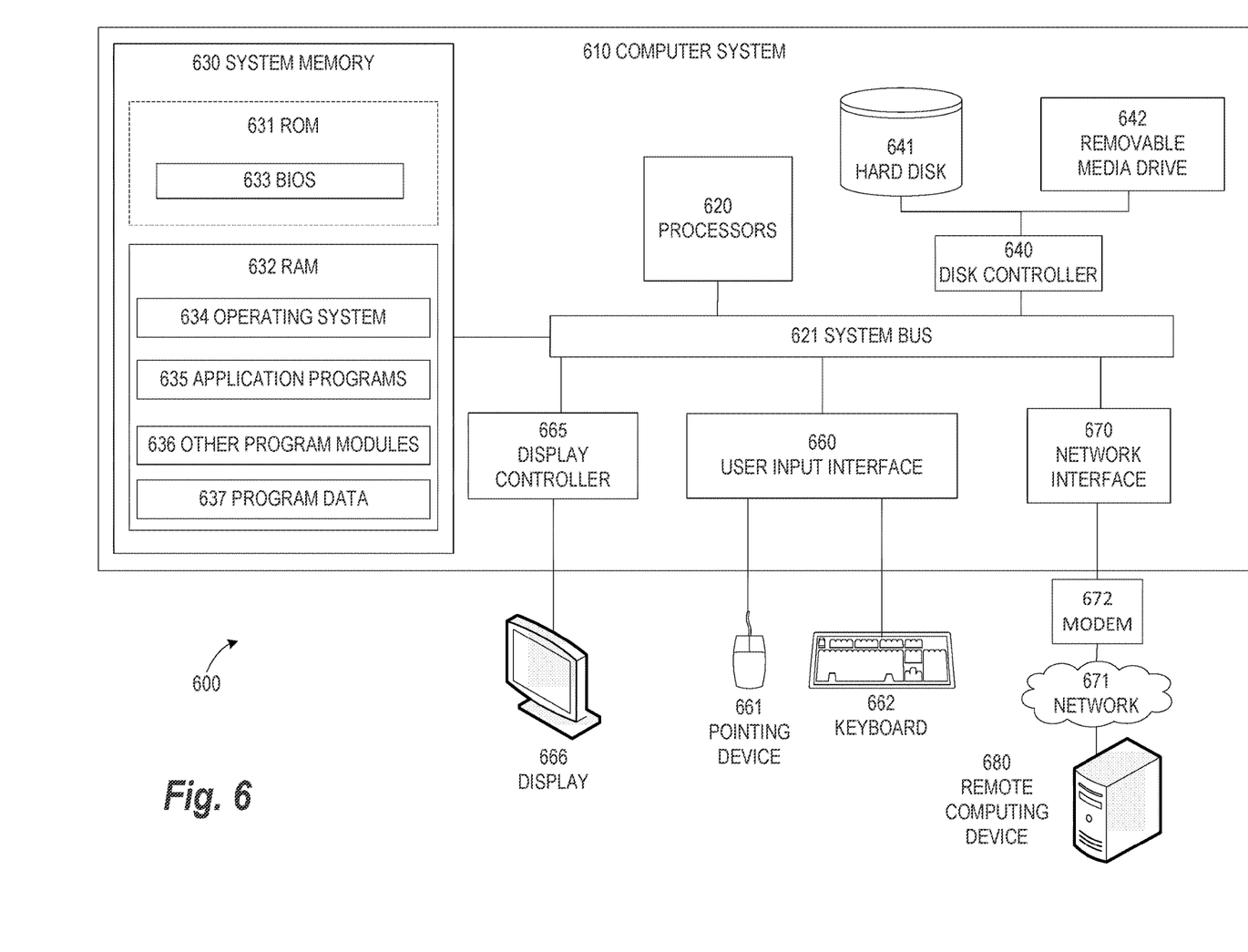
FIG. 6 illustrates an exemplary computing environment within which embodiments of the invention may be implemented.

FIG. 6 illustrates an exemplary computing environment 600 within which embodiments of the invention may be implemented. For example, this computing environment 600 may be used to train and execute the predictive models shown in FIG. 2 or to implement the method 400 shown in FIG. 4. The computing environment 600 may include computer system 610, which is one example of a computing system upon which embodiments of the invention may be implemented. Computers and computing environments, such as computer system 610 and computing environment 600, are known to those of skill in the art and thus are described briefly here.

As shown in FIG. 6, the computer system 610 may include a communication mechanism such as a bus 621 or other communication mechanism for communicating information within the computer system 610. The computer system 610 further includes one or more processors 620 coupled with the bus 621 for processing the information. The processors 620 may include one or more central processing units (CPUs), graphical processing units (GPUs), or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device (s) (e.g., programmable ROM, erasable PROM, and electrically erasable PROM). In addition, the system memory 630 may be used for storing temporary variables or other intermediate information during the execution of instructions by the processors 620. A basic input/output system 633 (BIOS) containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display 666, such as a cathode ray tube (CRT) or liquid crystal display (LCD), for displaying information to a computer user. The computer system includes an input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 642. The hard disk 641 may contain one or more datastores and data files used by embodiments of the present invention. Datastore contents and data files may be encrypted to improve security. The processors 620 may also be employed in a multi-processing arrangement to execute the one or more sequences of instructions contained in system memory 630. In alternative embodiments, hardwired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computer 680). The network 671 may be wired, wireless, or a combination thereof. Wired connections may be implemented using Ethernet, Universal Serial Bus (USB), RJ-11, or any other wired connection generally known in the art. Wireless connections may be implemented using Wi-Fi, WiMAX, and Bluetooth, infrared, cellular networks, satellite, or any other wireless connection methodology generally known in the art. Additionally, several networks may work alone or in communication with each other to facilitate communication in the network 671.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes, and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method for deriving biopsy results in a non-invasive manner, the method comprising:
   acquiring a plurality of training data items, wherein (i) each training data item comprises non-invasive patient data and one or more biopsy derived scores associated with an individual and (ii) the non-invasive patient data comprises one or more medical images;
   synthetically augmenting the training data items by applying deformations to each medical image;
   applying a segmentation algorithm to segment an organ included in the one or more medical images and associated with a particular disease, wherein the segmentation algorithm outputs a segmented organ comprising a plurality of disjoint organ segments;
   extracting a plurality of features from the non-invasive patient data based on the one or more biopsy derived scores, wherein the plurality of features is extracted based on the disjoint organ segments;
   training a first deep learning system to generate a predicted biopsy score based on the plurality of features and the one or more biopsy derived scores, wherein (i) the first deep learning system comprises a plurality of predictive models; (ii) each predictive model is trained with a distinct subset of the features; and (iii) the predicted biopsy score is a weighted combination of outputs generated by the plurality of predictive models;
   determining a plurality of model parameters associated with the trained first deep learning system; and
   delivering the plurality of model parameters to an image scanner to be used for configuration of a new second deep learning system on the image scanner.

2. The method of claim 1, further comprising:
   acquiring new non-invasive patient data corresponding to a new individual;
   extracting a plurality of new features based on the new non-invasive patient data; and
   generating a new predicted biopsy score for the new individual by applying the second deep learning system to the plurality of new features.

3. The method of claim 1, further comprising:
   acquiring new non-invasive patient data corresponding to a new individual, the new non-invasive patient data comprising one or more images;
   extracting a plurality of new features based on the new non-invasive patient data;
   generating a disease probability map for the new individual by applying the second deep learning system to the plurality of new features; and
   displaying the disease probability map overlaid on the one or more images.

4. The method of claim 1, further comprising:
   prior to extracting the plurality of features, localizing each of the one or more medical images to a region of interest associated with the particular disease,
   wherein the plurality of features is extracted based on the region of interest.

5. The method of claim 1, wherein the plurality of features comprises features automatically generated by applying a deep learning technique to the plurality of training data items.

6. The method of claim 1, wherein the plurality of features comprise features manually specified by one or more users.

7. The method of claim 1, wherein the non-invasive patient data further comprises at least one of clinical information associated with the individual or demographic data acquired from the individual.

8. The method of claim 7, wherein the non-invasive patient data further comprises at least one of in-vitro diagnostic data acquired from the individual.

9. A method for deriving biopsy results in a non-invasive manner, the method comprising:
   configuring, by an image scanner device, a deep learning system based on one or more model parameters received from a source external to the image scanner device;
   acquiring, by the image scanner device, a plurality of medical images of an anatomical area of interest;
   applying a segmentation algorithm to segment an organ included in the plurality of medical images and associated with a particular disease, wherein the segmentation algorithm outputs a segmented organ comprising a plurality of disjoint organ segments;
   extracting, by the image scanner device, a plurality of features from the plurality of medical images, wherein the plurality of features is extracted based on the disjoint organ segments; and
   generating, by the image scanner device, a single predicted biopsy score for a disease by applying the deep learning system to the plurality of features, wherein the single predicted biopsy score is generated by (a) determining a local biopsy score for each of the disjoint organ segments using a weighted combination of outputs generated by the plurality of predictive models and (b) combining the local biopsy scores to generate the single predicted biopsy score.

10. The method of claim 9, wherein the disease is prostate cancer and the single predicted biopsy score comprises a Gleason score.

11. The method of claim 9, wherein the plurality of medical images comprises (a) one or more anatomical images, and (b) one or more functional images.

12. The method of claim 11, wherein the plurality of medical images are acquired using a multi-parametric Magnetic Resonance / Positron Emission Tomography acquisition.

13. A system for deriving biopsy results in a non-invasive manner, the system comprising:
   an image scanner device configured to acquire one or more medical images of an anatomical area of interest; and
   one or more computer systems comprising:
      a deep learning system configured based on one or more model parameters received from a source external to the computer systems;
      one or more non-transitory, tangible computer-readable mediums holding computer-executable instructions for:
         applying a segmentation algorithm to segment an organ included in the one or more medical images and associated with a particular disease, wherein the segmentation algorithm outputs a segmented organ comprising a plurality of disjoint organ segments;
         extracting a plurality of features from the one or more medical images,
         wherein the plurality of features is extracted based on the disjoint organ segments; and
         generating a single predicted biopsy score for a disease by applying the deep learning system to the plurality of features, wherein the single predicted biopsy score is generated by (a) determining a local biopsy score for each of the disjoint organ segments using a weighted combination of outputs generated by the plurality of predictive models and (b) combining the local biopsy scores to generate the single predicted biopsy score; and one or more processors configured to execute the computer-executable instructions.

14. The system of claim 13, wherein the one or more computer systems are located in the image scanner device.

15. The system of claim 13, wherein the one or more computer systems are physically separated from the image scanner device.

16. The system of claim 13, wherein extraction of the plurality of features is performed by a first computer located in the image scanner device and generation of the single predicted biopsy score is performed at a second computer that is physically separated from the image scanner device.

* * * * *